United States Patent [19]
Bogert et al.

[11] Patent Number: 6,096,012
[45] Date of Patent: Aug. 1, 2000

[54] COATED ONE-PIECE COMPOSITE PLASTIC CATHETER AND CANNULA

[75] Inventors: David L. Bogert, Plainville; Zino Altman, Unionville, both of Conn.

[73] Assignee: Johnson & Johnson Medical, Inc., Arlington, Tex.

[21] Appl. No.: 08/703,707

[22] Filed: Aug. 27, 1996

[51] Int. Cl.[7] .................................................. A61M 25/00
[52] U.S. Cl. ............................................ 604/264; 604/524
[58] Field of Search ...................... 604/264, 265, 604/272, 273, 280, 281, 282, 239, 524

[56] References Cited

U.S. PATENT DOCUMENTS

| | | | |
|---|---|---|---|
| 2,217,602 | 10/1940 | Smith | 604/272 |
| 3,093,134 | 6/1963 | Roehr | 604/272 |
| 4,838,877 | 6/1989 | Massau | 604/272 |
| 4,840,622 | 6/1989 | Hardy | 604/280 |
| 4,882,777 | 11/1989 | Narula | 604/281 |
| 4,935,017 | 6/1990 | Sylvanowicz | 604/281 |
| 4,986,814 | 1/1991 | Burney et al. | 604/281 |
| 5,037,403 | 8/1991 | Garcia | 604/281 |
| 5,183,470 | 2/1993 | Wetterman | 604/281 |
| 5,452,726 | 9/1995 | Burmeister et al. | 604/281 |
| 5,453,099 | 9/1995 | Lee et al. | 604/282 |
| 5,634,913 | 6/1997 | Stinger | 604/272 |

*Primary Examiner*—Sharon Kennedy

[57] ABSTRACT

A one-piece or unitarily constructed composite plastic catheter and cannula arrangement and method of producing the arrangement, having a suitably coated needle point which is thereby facilitated for insertion thereof into the vein or body of a patient, whereby the arrangement of an inexpensively produced construction renders the composite catheter and cannula structure of a nature adapted to be readily disposable after only a single use and therefore economically viable, especially for undeveloped or developing countries or regions.

8 Claims, 1 Drawing Sheet

COATED ONE-PIECE COMPOSITE PLASTIC CATHETER AND CANNULA

BACKGROUND OF THE INVENTION

Field of the Invention

The present invention relates, in general, to intravenous catheter insertion devices, and in particular pertains to a coated unitarily constructed composite plastic catheter and cannula arrangement. More particularly, the invention is directed to the provision of a one-piece or unitarily constructed composite plastic catheter and cannula arrangement having a suitably coated needle point which is thereby facilitated for insertion thereof into the vein or body of a patient, whereby the arrangement of an inexpensively produced construction renders the composite catheter and cannula structure of a nature adapted to be readily disposable after only a single use and therefore economically viable, especially for undeveloped or developing countries or regions.

The invention is further directed to novel and unique methods of forming the unitary or single-piece coated composite plastic catheter and cannula arrangement, which are simple to implement and thereby rendering the manufacturing process thereof inexpensive so as to be particularly adapted for economical mass-production techniques for developing countries or regions.

The utilization of clinical apparatus in which pointed hollow needles or cannulae are employed in order to puncture the skin of a patient, and especially catheters utilizing such needles to effectuate venipunctures, is well known in the medical art and is widely practiced by physicians and clinical personnel for the purpose of injecting fluids and drugs directly into the bloodstream of patients. Additionally, during surgical operations or procedures it may be frequently required that whole blood transfusions and parenteral fluids be administered to a patient undergoing such surgical procedures. Basically, as is well known and has been employed for a considerable length of time, the introduction of such fluids into the cardiovascular systems of patients has necessitated the forming of a venipuncture utilizing a hollow rigid needle having a proximal attachment site for a fluid connection which is adapted to interconnect the needle with a source of intravenously administered fluids.

The foregoing method of administering fluids to patients through venipunctures has been subject to some rather serious problems in the administration of fluids to patients in this medical technology. Thus, a primary concern which had to be addressed resided in the inherent rigidity of the needle, the latter of which is normally generally constituted of surgical-quality steel, and while inserted into the vein of a patient, necessitated the needle to be maintained for reasons of safety in a fixed position at the general site of the venipuncture throughout the duration of fluid administration of transfusion, whereby such a procedure could conceivably consume a considerable length of time. In addition to the foregoing, at times it has been necessary to periodically draw blood samples and/or successively administer intravenous fluids to a patient, thus requiring the patient to be subjected to a series of plurality of venipunctures, each administered at a specific time and at different sites on the body, resulting in a relatively traumatic experience to the patient in view of such repeated and somewhat painful and unpleasant venipunctures. Particularly in developing or so-called "third world" countries is it the tendency to reuse a steel cannula, frequently referred to as a steel stylet catheter, many times over. This, notwithstanding the sterilizing and/or autoclaving of such steel stylet in the form of catheters and cannulae, dramatically increases the danger of infections to subsequent patients treated with such reused devices, and also exposes medical or clinical personnel to so-called "needle stick" by a potentially infected cannula upon the latter having been withdrawn from the body of a patient.

Inasmuch as the needle which has been previously positioned in the body of the patient upon forming the venipuncture may have been exposed to infectious agents; for instance, such as a patient infected with Acquired Immune Deficiency Syndrome (AIDS) which is frequently or practically always ultimately fatal in nature, or other dangerous infectious conditions such as hepatitis, notwithstanding the implementation of sterilizing procedures upon withdrawal of the needle from a patient, which in particular in developing countries may be rather rudimentary or crude in nature, there is present the danger or hazard that the clinical personnel may inadvertently or accidentally jab or stick themselves with the used needle after withdrawal from the body of the patient, with the possibility of infection or even death resulting therefrom. Unfortunately, in many developing countries this dangerous aspect which is encountered through the repeated us of such needles is not seriously considered in that rather than contemplating the dangers of infection or potential death resulting therefrom, economic aspects are considered to be of primary concern.

In order to ameliorate or possibly even eliminate the foregoing problems which are encountered in the reuse of steel cannulae or needles; in essence, which may result in extreme discomfort to patients during periods in which such needles remain inserted and endanger the risks of infection by other patients and medical personnel through, the repeated use of the same needles, in the medical technology it has been more recently the practice to introduce a flexible tubular catheter of a low-friction material, such as a silastic or Teflon into the vein of a patient and to permit the catheter tube to remain in such a position over lengthier periods of time for purposes of; for example, periodically administering fluids, including parenteral fluids, blood/plasma transfusions, medications in liquid form and also for the collection of blood samples and the like. In this manner, the previously encountered trauma, extravasation, and infiltration caused by repeated venipunctures have been largely avoided, and the danger and discomfort to a patient of leaving a rigid needle in the body for a prolonged period of time has been generally overcome. Thus, in order to position the distal end of such a flexible catheter tube within the body cavity of a patient, such as a vascular cavity or vein, there is normally employed a cannula or hollow sharp-tipped needle for the purpose of forming the venipuncture. Thereafter, the flexible catheter tube, which is telescopically and slidably coaxially mounted on the outer circumference of the cannula or hollow needle so as to extend sleeve-like thereabout is advanced along the length of the needle into the vein subsequent to the needle having formed the venipuncture. Thereafter, the needle is adapted to be withdrawn from the interior of the catheter tube, while permitting the latter to remain within the body of the patient at the site of the venipuncture, and the needle is suitably discarded.

Although the foregoing utilization of flexible catheter tubes and cannulae of which the former is essentially constituted of a plastic material and the latter of steel, incorporates structure for retracting the withdrawn needle into a protective environment, such as a safety housing or the like, the overall construction is relatively complex and, especially in developing or so-called "third world" countries, may be considered too expensive to be considered a viable economical alternative to the multiple reuse of steel cannulae or stylets.

SUMMARY OF THE INVENTION

Consequently, in order to propagate the concept of eliminating the multiple reuse of steel cannulae, such as steel stylet, with all its attendant disadvantages and obvious health risks to patients and clinical personnel, while also concurrently eliminating the expense of the more complex steel cannula and plastic catheter arrangements which are constituted of multiple cooperative components, the present invention contemplates the provision of a disposable coated unitarily constructed or one-piece plastic catheter and cannula structure in which at least the leading or tip end forming a sharp needle point which is insertable into the body of the patient at the site of a venipuncture is coated with a hard material to facilitate insertion into the patient, while thereafter the material of the coated inserted plastic is preferably adapted to soften and possibly dull so as to reduce any discomfort to the patient, and upon being withdrawn from the body of the patient will reduce the potential danger of needle stick to medical or clinical personnel. The unitary construction of a plastic catheter and cannula or needle, and the forming of the needle tip through the utilization of a simple coating method, renders the entire construction extremely simple and resultingly inexpensive to manufacture, thus enabling the entire composite cannula/cathether structure to be disposed of in a highly economical manner after only a single use.

The foregoing is accomplished in that the composite catheter and cannula structure, referred to as a stylet, is molded or formed from a suitable plastic material, preferably of a nature in which the material is softenable after insertion into the body of a patient, while being biocompatible so as to enable a long dwelling period in the patient, and also with the relatively soft plastic reducing the danger of needle stick being encountered by medical or clinical personnel. Numerous types of plastic materials readily lend themselves to being molded or formed into the unitarily constructed composite catheter and cannula arrangement, and a coating material is then deposited onto the pointy leading end of the needle so as to impart stiffness and rigidity thereto to enable insertion thereof into the body of the patient. This coating material may be constituted of an amorphous vacuum-deposited diamond so as to impart to the needle tip a hardness, lubricity and strength necessary to penetrate the patient of the skin with a minimal force, thereby resulting in a minimum amount of discomfort to the patient.

Accordingly, it is an object of the present invention to provide a coated unitarily constructed composite plastic catheter and cannula structure.

Another object of the present invention is to provide a one-piece coated plastic catheter and cannula structure providing for a relatively soft plastic material having the leading tip end thereof coated with a suitable hard material for insertion into the body of a patient, and whereby the construction is simple and inexpensive so as to render it economically disposable after only a single use.

A further object of the present invention resides in the provision of a method for the forming of the coated one-piece plastic catheter and cannula structure as described herein.

BRIEF DESCRIPTION OF THE DRAWINGS

The foregoing and other advantages of the invention may now be more readily ascertained from the following detailed description of a preferred embodiment of the coated one-piece plastic catheter and cannula, taken in conjunction with the accompanying drawings; in which.

DETAILED DESCRIPTION OF A PREFERRED EMBODIMENT

Figure 1:
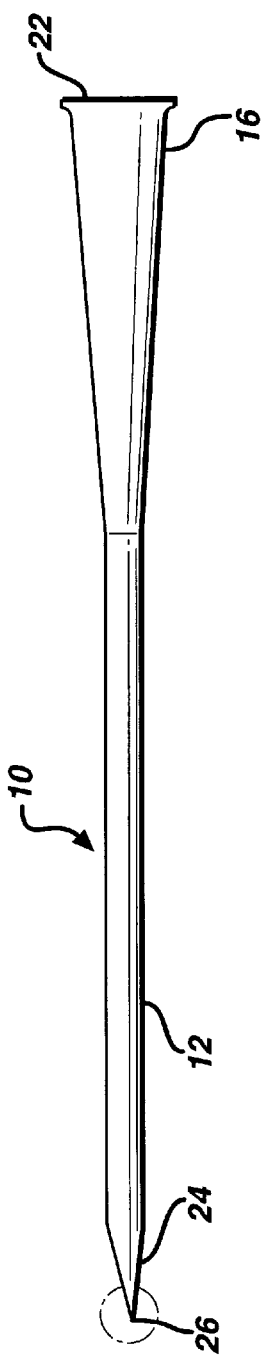
FIG. 1 illustrates a longitudinal view of a coated one-piece catheter and cannula pursuant to the invention.
Figure 2:
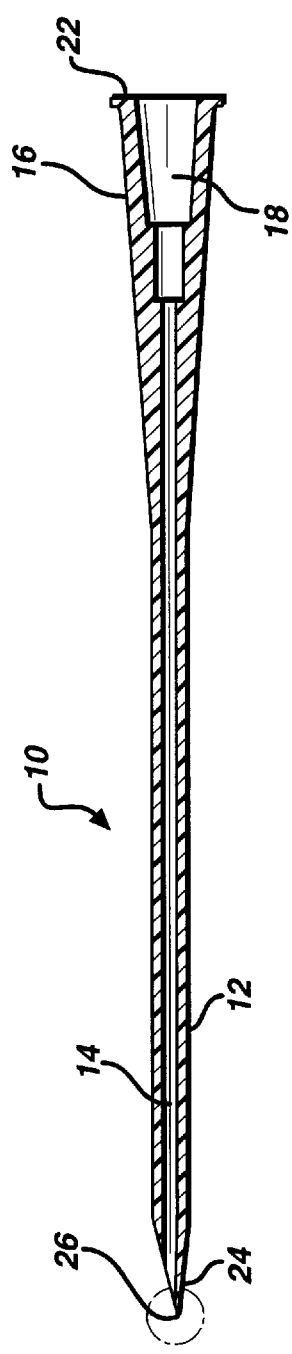
FIG. 2 illustrates a longitudinal sectional view of the catheter and cannula construction pursuant to FIG. 1.
Figure 3:
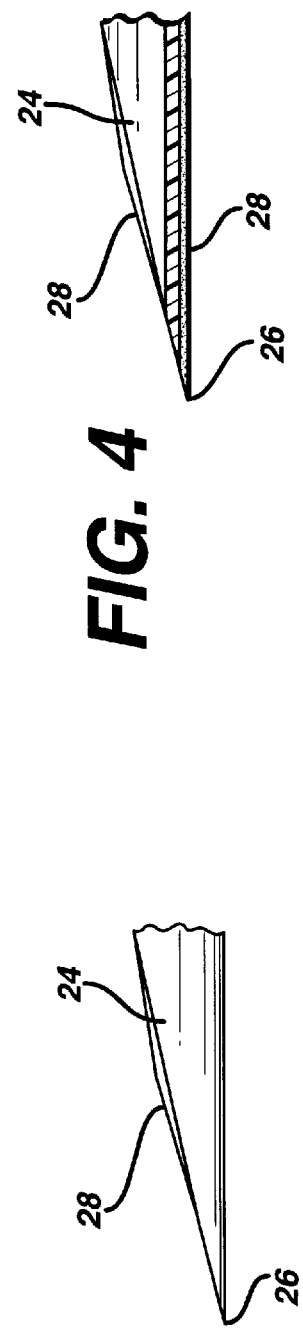
FIG. 3 illustrates, on an enlarged scale, the encircled coated tip or needle point portion of the plastic catheter and cannula construction pursuant to FIG. 1.
Figure 4:
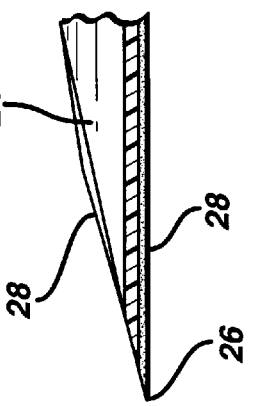
FIG. 4 illustrates in a view similar to FIG. 3 a sectional view of the needle tip portion of FIG. 2.

Referring now in particular to FIGS. 1 and 2 of the drawings there is illustrated a composite catheter and cannula arrangement 10 which consists of a unitary structure constituted from a plastic material.

The catheter and cannula arrangement 10 includes an elongate body 12 having a longitudinal central bore 14 for the flow therethrough of a blood supply or parenteral fluid adapted to be transmitted to a patient, or for withdrawing blood samples, and whereby one end 16 which is of a larger size in diameter which has a larger internal passageway 18 communicating with the longitudinal passageway or bore 14 extending through the length of the catheter/cannula body 12 is adapted to form a connector 22 to be attached to a suitable supply of fluid or blood, such as being connected by means of a Luer lock (not shown) or the like.

The leading or tip end 24 of the unitary or single-piece catheter/cannula or stylet arrangement 10 may be a V-point 26 so as to define the configuration of a hollow needle point which is readily insertable into the body of the patient, such as at the site of a venipuncture.

Inasmuch as the one-piece or unitarily contracted plastic material catheter/cannula arrangement is essentially soft or pliable in nature, in order to inpart a relatively stiff or rigid property to the needle tip, at that region the tip is coated to a thickness of about 0.01 to 50 nanometer, preferably by means of a high vacuum ion beam, with an amorphous diamond composition 28 which is adapted to impart to the needle-like tip end 24 of the catheter/cannula arrangement 10, a hardness, lubricity and strength which is necessary to penetrate the skin of a patient with the application of only minimal force, thereby causing the least amount of discomfort to the patient.

The plastic material for the unitary catheter and cannula arrangement 10, preferably, may be a "shape-memory" and/or "hydrogel" polyurethane, which may be provided individually or in a combination with each other, with the shape-memory polyurethane adapted to be molded so as to both soften and then return to a blunt point; in effect, be dulled, after insertion into the body of the patient. In clear contrast therewith, a hydrogel urethane would tend to absorb water or moisture once inserted into the body of the patient, both softening and dulling the tip or needle point 24, with a combination of the two types of urethanes also being applicable. These plastic materials would possess properties with various advantages such as (a) they are very biocompatible and could be in dwelling for lengthy periods of time in a patient without causing discomfort; (b) by softening and the dulling of the plastic material, these become even less irritating to the vein of the patient in which they are inserted; and (c) by softening and dulling of the plastic material, the chance of any potential needle stick upon withdrawal from the patient is reduced, thereby rendering the cannula/catheter arrangement 10 safer to medical personnel.

Other possible plastic materials applicable to the invention may comprise liquid crystal polymers, polyphenylene sulfide, epoxy, polyesters, polyolefins and polyamides, and the like.

These plastic materials can be readily molded through the intermediary of a plurality of injection molding techniques, including such as but not being limited to high pressure injection; for example at 30,000–50,000 psi; thermally cycled injection molding; compression molding; molding including a coining action; combined injection and compression molding; and molding by means of an oscillating molding component.

Furthermore, the sharp tip or needle point 24 of the catheter/cannula body 12 which is insertable into the patient and which is adapted to be coated with the high vacuum ion beam deposited amorphous diamond composition 28 can be molded at the same time as the body or tubular portion 12 of the catheter/cannula, or can be mechanically formed after molding, or can be laser cut after molding; andit is even possible to subsequently grind a sharp point on many of the various types of plastic material set forth herein.

With regard to the coating of the tip end 24, in lieu of amorphous diamond composition, it is also possible to contemplate other kinds of low temperature coatings embued with similar properties; and employing pointing methods, molding methods and base plastic materials in addition to those described hereinabove.

From the foregoing, it becomes readily apparent to one skilled in the art that the inventive coated one-piece plastic catheter/cannula arrangement 10 is extremely simple in design and use, and may be economically and inexpensively produced so as to render it suitable for mass-production techniques and particularly for use in developing or third world countries as disposable intravenous catheter insertion devices, thereby eliminating the need for the reuse of steel stylets and the therewith attendant and inherent dangers to the patients and medical personnel.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A unitary one-piece catheter and cannula constructed of composite plastic material comprising an elongated generally rigid tubular member having a first end of enlarged cross-sectional dimension forming a catheter hub structure and a second end distal from said first end having a sharp-tipped portion adapted to pierce and to be inserted into the body of a patient, wherein the outer surface of at least said second end encompassing said sharp-tipped portion is coated with a layer of a material imparting increased hardness, lubricity and strength enabling said sharp-tipped portion to penetrate the skin of a patient with minimal force.

2. A. A composite catheter and cannula as claimed in claim 1, wherein said coated material layer is constituted of amorphous diamond.

3. A composite catheter and cannula as claimed in claim 2, wherein said amorphous diamond forms a coating having a thickness within the range of about 0.01 to 50 nanometer.

4. A composite catheter and cannula as claimed in claim 2, wherein said amorphous diamond layer is formed through high-vacuum ion beam deposition.

5. A composite catheter and cannula as claimed in claim 1, wherein said plastic material comprises a shape-memory polyurethane.

6. A composite catheter and cannula as claimed in claim 1, wherein said plastic material comprises a hydrogel-based polyurethane.

7. A composite catheter and cannula as claimed in claim 1, wherein said plastic material comprises a composite shape-memory and hydrogel-based polyurethane.

8. A composite catheter and cannula s claimed in claim 1, wherein said plastic material is selected from the group of materials consisting of liquid crystal polymers, polyphenylene sulfide, epoxy, polyesters, polyolefins and polyamdies.

* * * * *